United States Patent

Tran

[11] Patent Number: 5,910,008
[45] Date of Patent: Jun. 8, 1999

[54] ARCHWIRE WITH POSTS

[75] Inventor: Khoa Q. Tran, Bristol, Conn.

[73] Assignee: Acme-Monaco Corporation, Plainville, Conn.

[21] Appl. No.: 09/031,171

[22] Filed: Feb. 26, 1998

[51] Int. Cl.⁶ .................................................. A61C 7/00
[52] U.S. Cl. ............................................. 433/22; 433/20
[58] Field of Search .................................. 433/17, 20, 22

[56] References Cited

U.S. PATENT DOCUMENTS

| Re. 35,170 | 3/1996 | Arndt et al. . | |
| 1,361,661 | 12/1920 | Alexander | 433/22 |
| 3,683,502 | 8/1972 | Wallshein | 433/22 |
| 3,893,241 | 7/1975 | Moriarty . | |
| 4,037,324 | 7/1977 | Andreasen . | |
| 4,571,179 | 2/1986 | Balenseifen | 433/20 |
| 4,583,944 | 4/1986 | Hanson . | |
| 4,639,219 | 1/1987 | Gagin . | |
| 5,064,370 | 11/1991 | Jones . | |
| 5,167,499 | 12/1992 | Arndt et al. . | |
| 5,306,142 | 4/1994 | Richards . | |
| 5,399,087 | 3/1995 | Arndt . | |
| 5,538,422 | 7/1996 | Arndt . | |
| 5,683,245 | 11/1997 | Sachdeva et al. . | |

*Primary Examiner*—Ralph A. Lewis
*Attorney, Agent, or Firm*—Pepe & Hazard, LLP

[57] ABSTRACT

An archwire is comprised of an elongated wire of nickel/titanium alloy in a generally arcuate configuration and a pair of tubular metallic sleeves in spaced apart relationship at predetermined points along the length of the wire. The sleeves are crimped onto the wire, and an upstanding metallic post is bonded on each of the sleeves. The posts are seated in the crimped area of the archwire and are secured thereto by brazing. The crimp formation is then heat set.

19 Claims, 2 Drawing Sheets

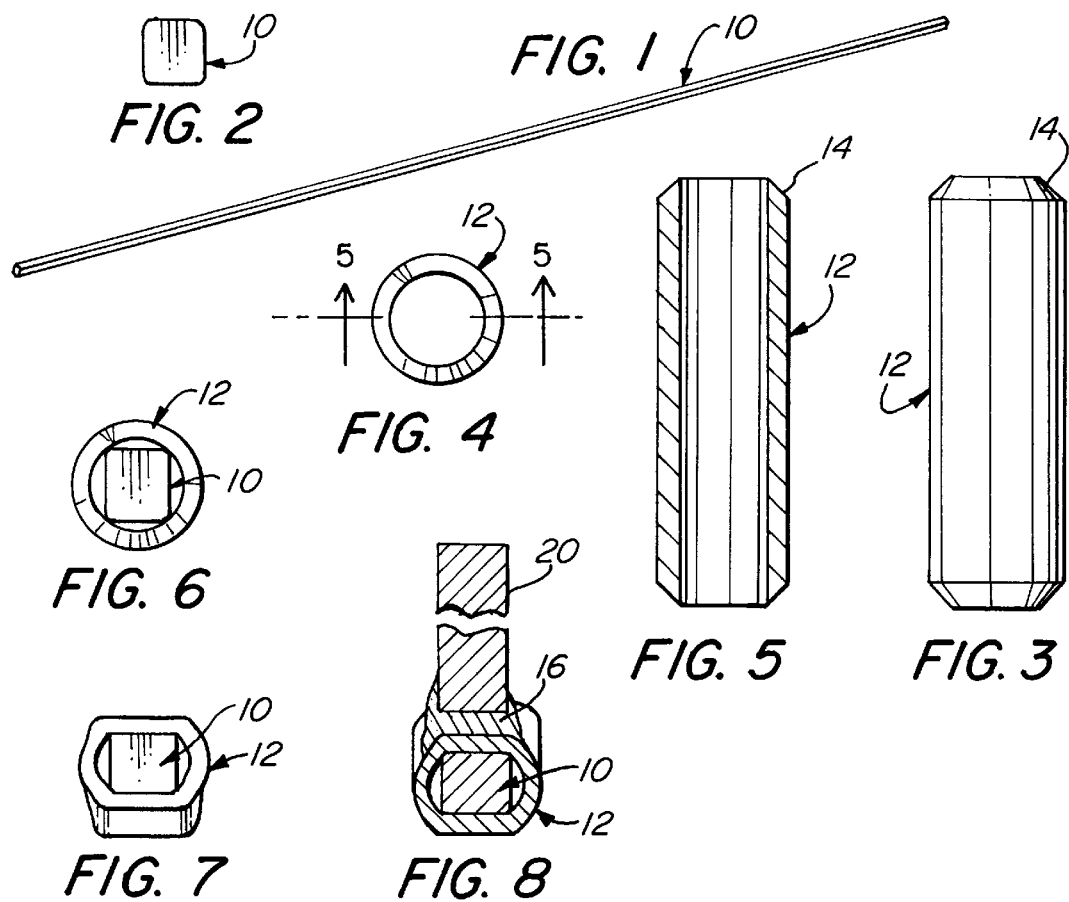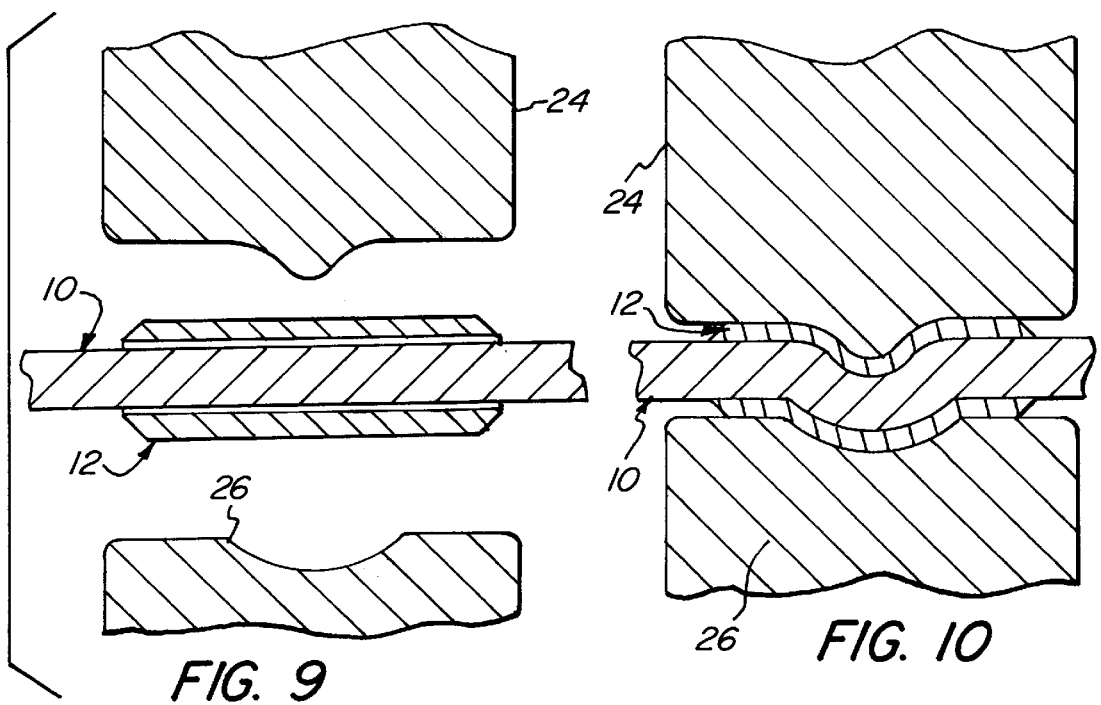

ARCHWIRE WITH POSTS

BACKGROUND OF THE INVENTION

The present invention relates to dental archwires, and, more particularly to archwires of nickel/titanium alloys which are provided with posts for engagement with orthodontic devices to provide restorative forces in orthodonture.

As is well known, highly resilient wire is employed in fabricating archwires for orthodontic applications in order to apply the desired force for the intended correction. These archwires must be secured to the orthodontic appliances affixed to the teeth, and it is generally desirable to provide posts on the wires for doing so.

Nickel/titanium alloys are considered particularly desirable for such operations because they may be preset in a configuration and a resultant "memory" as to this configuration to which the wire will attempt to return. Such nickel/titanium archwires provide a high degree of elasticity, generate a controllable force over an extended period of time, and exhibit biological inertness. However, efforts to secure posts directly to the nickel/titanium wire have not been satisfactory because the heat required to weld the posts to the wire destroys the memory and other desired properties of the wire, at least in the area where the welding is being performed.

Andreasen U.S. Pat. No. 4,037,324 describe the use of such alloys in fabricating archwires and the advantages which they afford in orthodontic appliances. Generally, such nickel/titanium alloys have a near stoichiometric composition of nickel titanium and may include small amounts of metals such as cobalt, tantalum, chromium/molybdenum to provide stiffness for some applications.

It is an object of the present invention to provide a novel archwire fabricated from nickel/titanium alloy wire on which posts are firmly secured at desired positions along the length thereof.

It is also an object to provide such an archwire in which the memory characteristics of the preset wire are used to enhance the security of the placement of the posts upon the archwire.

Another object is to provide a novel method for making such archwires utilizing easily assembled components to provide a rugged and long-lived assembly.

SUMMARY OF THE INVENTION

It has now been found that the foregoing and related objects may be readily attained in an archwire comprised of an elongated wire of nickel/titanium alloy and having a generally arcuate configuration. A pair of tubular metallic sleeves is provided in spaced apart relationship at predetermined points along the length of the wire, and the sleeves are crimped thereon. An upstanding metallic post is provided on each of the sleeves, and the posts are bonded to the sleeves.

Usually, the wire is of arched configuration with an arcuate central portion and generally rectilinear end portions. The sleeves are disposed on the arcuate central portion equidistantly on either side of the center of the central portion.

Desirably the wire is of rectangular cross section and the sleeves are of cylindrical configuration with chamfered ends. The sleeves have a dimple at the point of the crimp, and the posts are brazed to the sleeves at the crimp.

Desirably, the posts are fabricated from brass or stainless steel, and the sleeves are fabricated from stainless steel.

In the method for making the dental archwire, a pair of tubular metallic sleeves is slid onto a length of nickel/titanium wire and positioned at predetermined spaced positions along the length thereof. The sleeves are crimped onto the wire at the positions, and upright posts are secured to the sleeves.

Generally, the wire is preformed into a generally arch-like configuration with an arcuate center portion and the sleeves are disposed on the arcuate center portion equidistantly from the center thereof. The wire is heat treated to set the arch-like configuration prior to sliding the sleeves thereon, and the crimped wire and sleeves are heat treated prior to the step of securing the posts to set the crimped configuration.

BRIEF DESCRIPTION OF THE DRAWINGS

FIG. 1 is a perspective view of a wire utilized in making the archwires of the present invention;

FIG. 2 is a cross sectional view thereof;

FIG. 3 is a plan view of a sleeve utilized in making the archwires of the present invention;

FIG. 4 is a end elevational view thereof;

FIG. 5 is a sectional view thereof along the lines 5—5 of FIG. 4;

FIG. 6 is a cross sectional view of a sleeve about the wire prior to the crimping operation;

FIG. 7 is a similar cross sectional view after the crimping operation;

FIG. 8 is a similar cross sectional view thereof showing the post brazed thereon;

FIG. 9 is a fragmentary view of the wire of FIG. 1 with a sleeve of FIG. 3 disposed thereon and with crimping tooling disposed above and below the sleeve;

FIG. 10 is a similar view showing the tooling after effecting crimping of the sleeve and wire;

DETAILED DESCRIPTION OF THE ILLUSTRATED EMBODIMENTS

Figure 13:
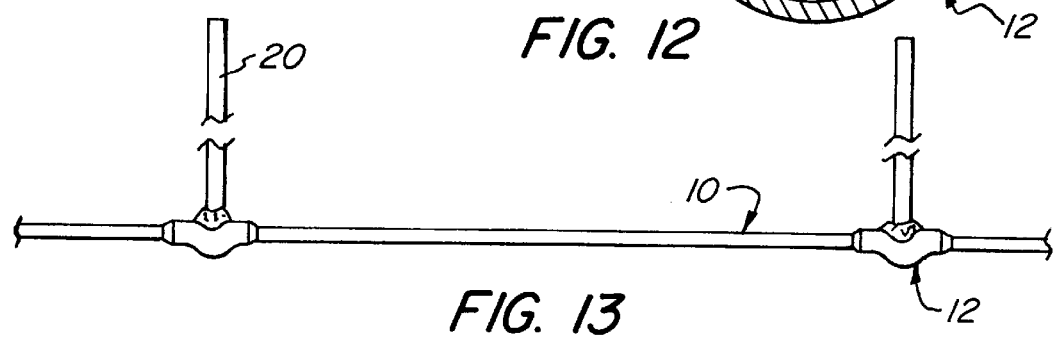
FIG. 13 is a fragmentary front elevational view of the assembled archwire, sleeves and posts.
Figure 14:
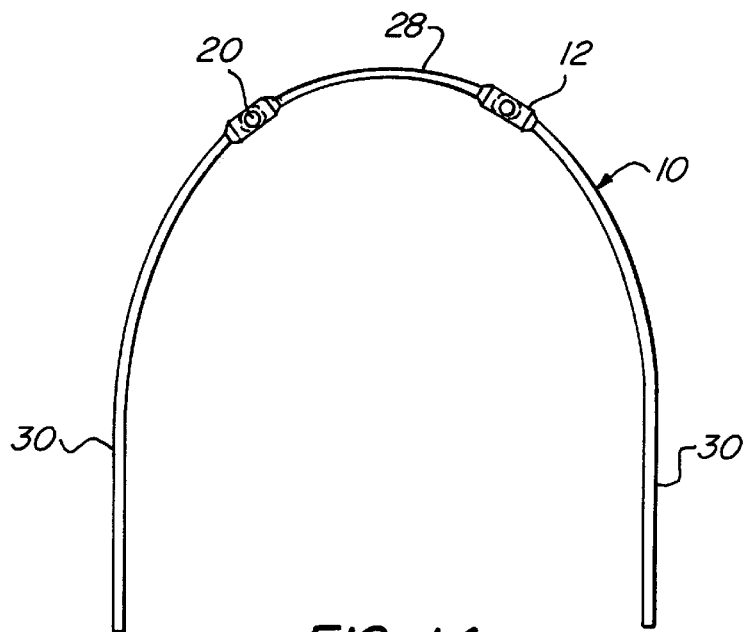
FIG. 14 is a plan view of the assembled archwire.

Turning first to FIGS. 13 and 14, therein illustrated is a dental archwire produced in accordance with the present invention comprising an elongated wire generally designated by the numeral 10 formed into an arch-like configuration with an arcuate center portion 28 and rectilinear end portions 30. Spaced to opposite sides of the center of the arcuate center portion 28 is a pair of sleeves generally designated by the numeral 12 with metallic posts 20 extending upwardly therefrom.

As seen in FIGS. 1 and 2, the wire is produced from a length of nickel titanium alloy of solid cross section usually rectangular. The sleeves 12 are of tubular cylindrical cross section and preferably have chamfered ends 14. The sleeves 12 are located at predetermined points along the length of the wire 10 at which they are crimped to secure them in their predetermined positions as shown in FIG. 11.

Figure 11:
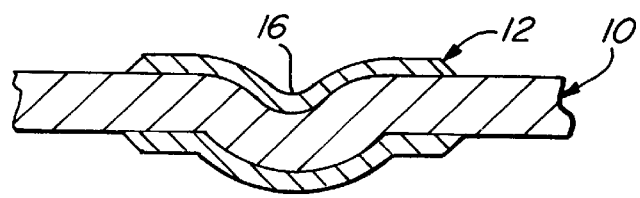
FIG. 11 is a fragmentary longitudinal sectional view of the archwire following crimping of the sleeve thereon.

As seen in FIGS. 7 and 11, the crimping process produces a dimple 18 on the upper surface, and the metallic wire posts 20 are inserted into the dimples 18 and secured thereto by a braze 22.

As seen in FIGS. 9 and 10, crimping tools having an upper component 24 and a lower component 26 are utilized to effect the crimping of the sleeves 12 onto the wire 10. When the tools are moved towards each other as seen in FIG. 10, a crimp or deformation of the sleeve 12 and wire 10 is formed to produce the dimple 18 in the upper surface of the wire/sleeve assembly.

Generally, the wire 10 is formed into the desired arch-like configuration prior to the assembly of the sleeves 12 thereon, and this configuration is set by heat treatment at a temperature of about 476–486° C. for 5–7 minutes. After the sleeves have been slid thereonto and crimped in position, the crimp configuration is set by exposing the wire/sleeve assembly to a temperature of 454–482° C. for 2–3 seconds. The soldering process will not effect the heat set of the crimped offset configuration.

Figure 12:
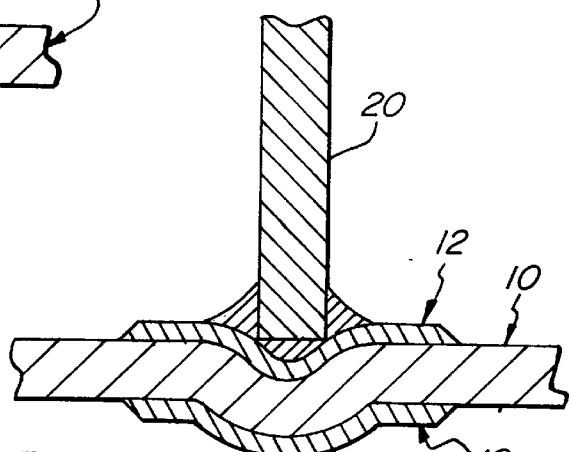
FIG. 12 is a fragmentary longitudinal sectional view of the archwire with a fragmentarily illustrated post brazed thereon.

The posts 20 are precut to the desired length and positioned in the dimples 18, conveniently in a suitably configured jig. A braze 22 is applied about the base of the parts 20 to produce the structure seen in FIG. 12.

As is well known, nickel/titanium wire has a very high degree of superelasticity and has memory characteristics, both of which would be adversely impacted in the event that the archwire were subjected to a high temperature. The cross section can be circular or rectangular. The tubular sleeve 12 allows the crimping or staking operation to effect mechanical engagement between the sleeve 12 and the underlying wire 10, and this deformation can then be fixed by subsequent heat treatment for a very short period which does not affect the heat set of the arched configuration.

In the brazing or welding step to secure the posts 20 to the sleeve 12, the sleeve 12 itself acts as a heat sink and dissipates the heat over a large surface area so that it does not affect the memory characteristics of either the offset or the properties of the underlying wire.

Illustrative of the practice of the present invention is the following example:

Example One

A length of nickel/titanium (45/55 percent) wire 7 inches in length with a rectangular cross section 0.019×0.025 inch is formed into an arch with a spacing of 2⅜ inch between its rectilinear end portions. The configuration is set by heat treatment at 480° C. for 6 minutes.

Cylindrical tubes of 0.120 inch in length and having an inside diameter of 0.030 inch and chamfered ends are slid onto the wire and positioned on either side of the center to provide a center to center spacing of 1.2 inches. The sleeves are then crimped onto the wire to produce a dimple in the upper surface thereof as shown in the attached drawings and the wire with the sleeves is then subjected to heat treatment at 850–900° F. for 2–3 seconds to heat set the offset which has been produced by the crimping operation.

Lastly, posts of 0.032 inch diameter Type 304 stainless steel wire annealed to dead soft condition are placed in the area of the dimples and brazed with a zinc/nickel/copper braze sold by Fusion Incorporated of Willoughby, Ohio under the designation STN-1260-651.

Testing of the assembly establishes that the posts are firmly secured in position and that the basic wire retains it high elasticity and memory characteristics.

Although various materials may be utilized for the tubular sleeves, Type 304 stainless steel annealed to a dead soft condition has been found particularly advantageous since it is biologically inert, strong and resistant to corrosion while enabling the crimping operation to be carried out readily.

The posts themselves can be fabricated from Type 304 stainless steel which is annealed to a dead soft condition, or brass, or any other metal which enables it to be bent readily for the subsequent operations in the orthodontic appliance and which can be bonded by brazing or soldering to the underlying tubes.

Thus, it can be seen from the foregoing detailed description and attached drawings that the method of the present invention provides a novel dental archwire which is easily utilized and long lived. The components are readily assembled by a simple and effective process which maintains the desirable characteristics of the underlying nickel/titanium wire.

Having thus described the invention, what is claimed is:

1. A dental archwire comprising:

(a) an elongated wire of nickel/titanium alloy and having a generally arcuate configuration;

(b) a pair of tubular metallic sleeves in spaced apart relationship at predetermined points along the length of said wire, said sleeves being crimped onto said wire and providing a crimped cross section intermediate the length thereof; and (c) an upstanding metallic post on each of said sleeves, said posts being bonded to said sleeves at said crimped cross section.

2. The dental archwire in accordance with claim 1 wherein said wire is of arched configuration with an arcuate central portion and generally rectilinear end portions.

3. The dental archwire in accordance with claim 2 wherein said sleeves are disposed on said arcuate central portion equidistantly on either side of the center of said central portion.

4. The dental archwire in accordance with claim 1 wherein said wire is of rectangular cross section.

5. The dental archwire in accordance with claim 4 wherein said sleeves are of cylindrical configuration with chamfered ends.

6. The dental archwire in accordance with claim 1 wherein said crimped cross section of said sleeves provides a dimple.

7. The dental archwire in accordance with claim 6 wherein said posts are brazed to said sleeves at said dimple.

8. The dental archwire in accordance with claim 1 wherein said sleeves are fabricated from stainless steel.

9. The dental archwire in accordance with claim 8 wherein said posts are fabricated from brass.

10. The dental archwire in accordance with claim 8 wherein said posts are fabricated from stainless steel.

11. In a method for making a dental archwire, the steps comprising:

(a) sliding a pair of tubular metallic sleeves onto a length of nickel/titanium wire and positioning said sleeves at predetermined spaced positions along the length thereof;

(b) crimping said sleeves onto said wire at said positions to provide a crimped cross section intermediate the length thereof; and (c) bonding upright posts to said sleeves at said crimped cross section.

12. The method of making a dental archwire in accordance with claim 11 wherein said wire is preformed into a generally arch-like configuration with an arcuate center portion wherein said sleeves are disposed on said arcuate center portion equidistantly from the center thereof.

13. The method of making a dental archwire in accordance with claim 12 wherein said wire is heat treated to set said arch-like configuration prior to sliding said sleeves thereon.

14. The method of making dental archwire in accordance with claim 11 wherein said posts are fabricated of brass.

15. The method of making a dental archwire in accordance with claim 11 wherein said sleeves and said posts are fabricated from stainless steel.

16. The method of making a dental archwire in accordance with claim 11 wherein said crimping produces dimples in said sleeves and wherein said posts are brazed to said sleeves at said dimples.

17. The method of making a dental archwire in accordance with claim 11 wherein said crimped wire and sleeves are heat treated prior to the step of securing said posts to set the crimped configuration.

18. A dental archwire comprising:

(a) an elongated wire of nickel/titanium alloy and having a generally arcuate configuration;

(b) a pair of tubular metallic sleeves in spaced apart relationship at predetermined points along the length of said wire, said sleeves being crimped onto said wire and producing dimples at the point of said crimps; and (c) an upstanding metallic post on each of said sleeves, said posts being brazed to said sleeves at said dimple.

19. In a method for making a dental archwire, the steps comprising:

(a) sliding a pair of tubular metallic sleeves onto a length of nickel/titanium wire and positioning said sleeves at predetermined spaced positions along the length thereof;

(b) crimping said sleeves onto said wire at said positions, said crimping producing dimples in said sleeves; and (c) brazing upright posts on said sleeves at said dimples.

* * * * *